(12) United States Patent
Popp

(10) Patent No.: US 9,486,489 B2
(45) Date of Patent: Nov. 8, 2016

(54) METHOD FOR PRODUCING DRY EXTRACTS

(75) Inventor: Michael Popp, Lauf-Heuchling (DE)

(73) Assignee: Bionorica SE, Neumarkt (DE)

( * ) Notice: Subject to any disclaimer, the term of this patent is extended or adjusted under 35 U.S.C. 154(b) by 233 days.

(21) Appl. No.: 14/239,226

(22) PCT Filed: Aug. 20, 2012

(86) PCT No.: PCT/EP2012/066212
§ 371 (c)(1),
(2), (4) Date: May 21, 2014

(87) PCT Pub. No.: WO2013/026830
PCT Pub. Date: Feb. 28, 2013

(65) Prior Publication Data
US 2014/0271941 A1    Sep. 18, 2014

(30) Foreign Application Priority Data

Aug. 19, 2011  (EP) .................................... 11178206
Dec. 15, 2011  (EP) .................................... 11193734
May 30, 2012   (EP) .................................... 12170125

(51) Int. Cl.
| | | |
|---|---|---|
| A01N 65/00 | (2009.01) |
| A61K 36/35 | (2006.01) |
| A61K 36/85 | (2006.01) |
| A61K 36/185 | (2006.01) |
| A61K 36/515 | (2006.01) |
| A61K 36/70 | (2006.01) |

(52) U.S. Cl.
CPC ............. *A61K 36/35* (2013.01); *A61K 36/185* (2013.01); *A61K 36/515* (2013.01); *A61K 36/70* (2013.01); *A61K 36/85* (2013.01)

(58) Field of Classification Search
CPC .................................................... A61K 36/00

USPC ......................................................... 424/725
See application file for complete search history.

(56) References Cited

U.S. PATENT DOCUMENTS

| 5,939,071 A | 8/1999 | Joseph |
| 2004/0128852 A1 | 7/2004 | Joseph |
| 2010/0068273 A1 | 3/2010 | Popp |
| 2010/0323013 A1 | 12/2010 | Bonn et al. |

FOREIGN PATENT DOCUMENTS

| DE | 102005053926 B3 | 6/2007 |
| EP | 0753306 A1 | 1/1997 |
| EP | 1392337 A1 | 3/2004 |
| WO | WO-02073108 A1 | 9/2002 |

OTHER PUBLICATIONS

Translation of the International Preliminary Report on Patentability for PCT/EP2012/066212, dated Feb. 25, 2014.
"Basic Course in Drug Development XI, Methods for Producing Pharmaceutical Agents" (1971).
English translation of the International Search Report for PCT/EP2012/066212 mailed Nov. 23, 2012.

*Primary Examiner* — Michael Meller
(74) *Attorney, Agent, or Firm* — Drinker Biddle & Reath LLP

(57) ABSTRACT

The invention relates to a method for producing dry extracts of plants and to pharmaceutical preparations containing the same, more particularly phytopharmaceuticals, which contain at least one ethanolic/aqueous extract of a plant (drug), the plants being selected from the group consisting of: *Rumicis herba; Verbena officinalis; Sambucus nigra; Primula veris*; and *Gentiana lutea* and mixtures thereof. The invention further relates to a pharmaceutical for treating inflammatory and/or infectious diseases of the nose and throat area and/or the nasal sinuses, as well as the use thereof.

13 Claims, 9 Drawing Sheets

METHOD FOR PRODUCING DRY EXTRACTS

CROSS-REFERENCE TO RELATED APPLICATIONS

This application is a national stage application (under 35 U.S.C. §371) of PCT/EP2012/066212, filed Aug. 20, 2012, which claims benefit of European application 11178206.6, filed Aug. 19, 2011, European application 11193734.8, filed Dec. 15, 2011, and European application 12170125.4, filed May 30, 2012.

FIELD OF THE INVENTION

The invention relates to a method for producing dry plant extracts and to pharmaceutical preparations containing the same, in particular phytopharmaceuticals, which contain at least one ethanolic/aqueous extract of a plant (drug), wherein the plants are selected from the group consisting of: *Rumex acetosa* L., *Rumex acetosella* L., *Rumex obtusifolius* L., *Rumex patientia* L., and *Rumex crispus* L., (referred to hereinafter by the collective term "*Rumicis herba*"); *Verbena officinalis*; *Sambucus nigra*; *Primula veris*; and *Gentiana lutea* and mixtures thereof. The invention also relates to a pharmaceutical for treating inflammatory and/or infectious diseases of the nose and throat area and/or of the nasal sinuses, and to a dietary supplement, and also to the use thereof.

BACKGROUND OF THE INVENTION

The above medicinal plants are known as secretolytic agents in the case of infections of the upper airways, in particular in the case of sinusitis. Here, each individual drug contributes its share to the unique efficacy of the composition:

The root of *Gentiana lutea* (Gentian root) is generally used for medicinal purposes. Various secoiridoid glycosides with expectorant effect are found inter alia among the ingredients.

The leaves and stem of the aforementioned *Rumex* types, referred to hereinafter as "*Rumicis herba*" (Sorrel herb), are generally used for medicinal purposes. Flavonoids and various tanning agents are found herein as ingredients with anti-inflammatory effect, which additionally positively support the body's own defences.

The collective term "*Rumicis herba* (Sorrel herb)" is to be understood to mean a mixture of the following species:
*Rumex acetosa* L., synonym: *Lapathum acetosa* SCOP, synonym: *Lapathum pratense* LAM, synonym: *Acetosa pratensis* MILLER; *Rumex acetosella* L, synonym: *Rumex infestus* SALISB; *Rumex obtusifolius* L., synonym *Lapathum obtusifolium* MOENCH, synonym *Lapathum obtusantum* MONTAD, synonym *Rumex actus* WALLR, synonym *Rumex silvestris* WALLR;
*Rumex patientia* L., synonym *Rumex olympicus* BOISS., synonym *Lapathum hortense* MOENCH; *Rumex crispus* L.; *Rumex thyrsiflorus* FINGERH., synonym *Acetosa thyrsiflora* FINGERH, synonym *Rumex acetosa* subsp. *auriculatus* WALLR.

The leaves and stem of *Verbena officinalis* (Verbena herb) are preferably used for medicinal purposes and contain iridoid glycosides, phenylethanoid glycosides and flavonoids as primary ingredients, whereby expectorant and antiviral effects are achieved.

The leaves of *Sambucus nigra* (Elder flower, *Sambucus nigra* leaves) are typically used for medicinal purposes, of which the contents contain various flavonol glycosides and which contains sambunigrin, a cyanogenic glycoside, as a primary ingredient, which have an expectorant and antiviral effect (Grabovac, A. and Ullmer, A., Österreichische Apotheker-Verlagsgesellschaft m.b.H (Austrian Pharmacists' Publishing House), 2003).

Flowers and sepals of *Primula veris* (Primula flower, *Primula veris* leaves) are used for medicinal purposes. The ingredients comprise triterpene saponins and also phenol glycosides such as primulayerin. They have an expectorant effect and fight against viruses. The ingredients act as a mild secretolytic agent and expectorant in the case of treatment of respiratory diseases.

The combination of the aforementioned medicinal plants is known as a secretolytic agent under the trade name Sinupret®, which is registered for the applicant and has been available on the market for approximately 75 years. The medicinal plants used in Sinupret® are selected, tested and further processed in a targeted manner. The uniform quality of the pharmaceutical attained hereby is achieved by the manufacturer, the company BIONORICA, by optimized propagation and harvesting strategies and also by strict quality control.

The composition forming the basis of Sinupret® is preferably effective in the case of inflammation and also infections of the throat, nose and ear region, and is particularly suitable for the treatment of acute and chronic sinusitis and/or rhinosinusitis.

Both acute and chronic sinusitis are common. In three of four cases, the sinusitis develops as a result of a cold that spreads to the nasal sinuses and is accompanied by inflammation of the mucous membrane. The airways reach from the main nasal cavity to the various sinuses as far as the pulmonary alveoli. The nasal sinuses include the frontal sinus, the ethmoid sinus, the sphenoid sinus and the maxillary sinus. All of the aforementioned bone cavities are lined with mucous membrane and open out via narrow openings (the ostia) into the main nasal cavity.

The surface of the airways is coated with a protective mucus, to which dirt particles and pathogens, such as viruses, bacteria or funguses, which infiltrate together with the inhaled air, remain adhered. The mucus contains antibodies, which attack the infiltrating substances and make them harmless. So that the foreign substances can be flushed out from the body, the mucus is generally transported away with the aid of the cilia of the ciliated epithelium in the direction of the throat, where it can be swallowed. In order to fend off infection-induced respiratory diseases, the mucous membrane must have unhindered protective and cleaning mechanisms. In order to transport away the mucus charged with pathogens, the unhindered function of the cilia is indispensible, said cilia transporting the mucus further as a result of undulating movements. With infection and with inflammatory processes of the upper airways, the function of the protective and cleaning mechanisms of the mucous membrane is limited.

For example, viruses such as rhinoviruses, adenoviruses or coronaviruses trigger inflammatory reactions of the mucous membranes, whereby the mucous membrane becomes swollen and produces increased mucus. This initially results in aqueous and then viscous mucus flow. Over the course of inflammation of the nasal mucous membrane, the ostia of the sinuses may swell and impair or even prevent the discharge of the mucus. This leads to a blockage in the sinuses associated with viscous mucus, which leads to a deterioration of function or loss of function of the cilia. This ultimately causes a deterioration of the cleaning mechanism of the mucous membrane.

Such a microenvironment promotes the rapid increase of the ubiquitous microorganisms. Over a relatively long period of time, these unfavourable conditions, such as a swollen mucous membrane and cilia conglutinated by viscous mucus, this may lead to chronic sinusitis, resulting in permanent damage to the mucous membrane and to the ciliated epithelium. Pathogens relevant to the airways, which are also to be understood in particular to include ENO-relevant germs, which settle in the mucus, for example include *Staphylococcus aureus, Staphylococcus epidermidis, Streptococcus pyogenes, Streptococcus pneumoniae, Streptococcus mutans* or *Haemophilus influenzae.*

In the event that the upper airways become conglutinated as a result of viscous mucus, the ingredients of the used composition (*Gentiana lutea:Rumicis herba:Verbena officinalis:Sambucus nigra:Primula veris*=1:3:3:3:3) induce the formation of fresh, thin mucus, whereby the above-described process of expectoration and the transporting away and also reduction of the inflammatory symptoms is achieved and a healing process of the nasal mucous membrane is initiated. Sinupret® gently causes the re-establishment of the self-cleaning power of the airways and simultaneously develops a strong antimicrobial effect. Sinupret® is characterized by its good compatibility, composition established by BIONORICA and dosing, which rarely cause side effects in patients, and, in addition, no interactions with other pharmaceuticals are known.

Dry plant extracts are described in general and dry plant extracts formed from aqueous/ethanolic extracts are known.

Dry plant extracts can be produced for example in large amounts in accordance with the technical teaching of EP0753306.

However, there is a considerable need to provide a new Sinupret® dry plant extract, which has an advantageous improved effect of the plant combination.

The Deutsche Arzneimittelbuch (DAB or German Pharmacopoeia) 2010 establishes minimum contents of ingredients for drug quality, such that increased efforts have to be made for constant and improved quality. Extraction and drying methods specifically constitute a bottleneck for a sufficient quality of phytopharmaceuticals.

BRIEF SUMMARY OF THE INVENTION

Based on this prior art, the object of the present invention is therefore to provide an improved method for producing a dry plant extract and also an improved dry plant extract as such, which contains at least one ethanolic/aqueous extraction step, wherein the plants are selected from the group consisting of: *Rumex acetosa* L., *Rumex acetosella* L, *Rumex obtusifolius* L., *Rumex patientia* L., and *Rumex crispus* L., (referred to hereinafter and in the claims by the collective term "*Rumicis herba*"); *Verbena officinalis; Sambucus nigra; Primula veris*; and/or *Gentiana lutea* and mixtures thereof.

DETAILED DESCRIPTION OF THE INVENTION

Figure 1:
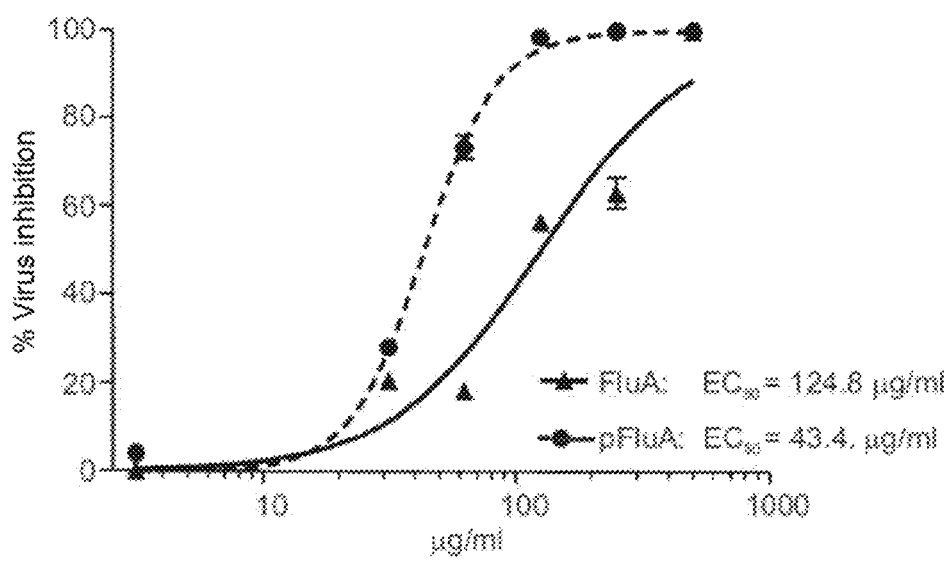
FIG. 1 shows the inhibition of human flu virus and pig flu virus proliferation.

Surprisingly, an improved dry plant extract could be obtained by means of a twofold extraction process, wherein, in a first step, an aqueous/ethanolic extraction took place, and, in a second step, an aqueous extraction took place.

Surprisingly, the content of advantageous active ingredients in existing active ingredient mixture in the respective overall extract can be enriched after drying by means of this method according to the invention, such that an improved pharmacological efficacy of the obtained dry plant extract is achieved.

The invention therefore relates to a method for producing dry plant extracts, said method comprising the following steps:
 a.) alcoholic/aqueous extraction of *Rumicis herba, Verbena officinalis, Sambucus nigra, Primula veris* and *Gentiana lutea,*
 b.) separation of the supernatant,
 c.) second aqueous extraction of the residue from a.),
 d.) separation of the supernatant,
 e.) combining of the obtained supernatants from b.) and d.),
 f.) drying of the supernatants and provision of the dry plant extract.

The improvement according to the method lies in the fact that a quicker efficacy is achieved compared to a conventional simple aqueous-ethanolic extract (see the examples). This is surprising since a linear extrapolation would have been expected at best as a result of a change of the solvent for extraction (for example if aqueous/ethanolic extraction is carried out exclusively or if aqueous extraction is carried out exclusively).

In particular, the method according to the invention allows an improved dosing, such that an increased curative effect can be achieved with the same dose.

The invention therefore likewise relates to a dry plant extract, which is obtained or is obtainable in accordance with a method according to the invention (hereinafter dry (plant) extract according to the invention, Sinupret dry extract (TE)).

In a further preferred embodiment of the method according to the invention, the ratio of *Gentiana lutea:Rumicis* herba:*Verbena officinalis*:*Sambucus nigra*:*Primula veris* is 1:3:3:3:3, in each case +/−0.3 to 0.5 (for example 1:3.2:2.9: 2.5:3.2:3).

Furthermore, it is preferable for a plant grouping of all plant (drugs) to be provided in a batch, wherein the ratio of plant (drugs) is as mentioned above. Furthermore, it is preferable for the presented plant (drugs) to be cleaned and cut.

In a further preferred embodiment of the method according to the invention, the aqueous/alcoholic extraction agent in step a.) has a content 40:60 (v/v) to 60:40 (v/v), in particular 41:59 (v/v) or 50:50 (v/v) of water/alcohol. Ethanol is preferred, however methanol and propanol or mixtures thereof are also included. Furthermore, the use of 96% ethanol is preferred.

In accordance with the invention, the extraction in steps a.) and c.) is also carried out at 20 to 40° C., wherein the extraction is carried out in steps a.) and c.) in 2 to 8 h.

Within the meaning of this invention, a "separation of the supernatant" can be carried out continuously or discontinuously after extraction in accordance with the invention by means of draining, decantation, filtration, screening or a separation method known to a person skilled in the art.

Furthermore, it is preferable for the drying according to step f.) to be carried out under vacuum at 30 to 60° C., in particular at 40 to 50° C., preferably in a vacuum agitated dryer. The dry extract according to the invention has a residual ethanol content of at most 0.5%.

Further suitable drying methods according to the invention will be explained:

Dry plant extracts are produced conventionally, wherein a plant material is extracted with the aid of a solvent or solvent mixture, for example by means of maceration or percolation, and, after separation of the extraction residue, the obtained fluid extract or the obtained tincture is compressed until dry.

Conventional drying methods are comprised in accordance with the invention and include fluidized bed drying or the compression to a thick or spissum extract and subsequent vacuum band drying or tray drying of said spissum extract.

Conventional methods for producing dry plant extracts according to the invention via a fluid extract (or liquid plant extract) or a tincture may likewise be considered; wherein, after subsequent distillation of the solvents, what is known as a spissum extract (viscose extract) is obtained, to which auxiliary agents and/or additives, such as lactose, polyvinylpyrrolidone, sucrose, silicon dioxide, etc., are often added. This moist, viscose mass is then introduced into tray cabinets or dryers for desired dry extract preparation.

A method that is very often used in dry extract production is what is known as the vacuum band drying method. In this case, the spissum extract is brought to dry extract preparation after preliminary drying via a downdraft vaporizer.

A drying method by means of a fluidized bed dryer requires temperatures between approximately 47° C. and 117° C. The drying process in this method is carried out under normal pressure conditions.

A gentle drying method for obtaining dry plant extracts according to the invention is described in EP 0 753 306. In accordance with the described method, the fluid extract from the plant materials obtained in the extraction is introduced in accordance with the method according to the invention in a vacuum drying system, preferably a vacuum agitated dryer with a multi-branched stirrer extending through a cylindrical mixing and drying chamber and having its own drive, and, where necessary, provided with vapour filter, backwash device, solvent condenser with aftercooler and collection vessel, back-condenser and a process, control and regulation unit, and optionally with granulation nozzles, and is dried in the dryer equipped with a chopper extending over the overall depth of the mixing and drying chamber and having blades rotating through a comb-shaped stator at a supply and return temperature between 120° C. and 5° C., an inner chamber temperature between 10° C. and 80° C., a filter temperature from 15° C. to 55° C., and a pressure between 0.5 1,000 mbar, and also a stirrer speed of rotation from 0 and 10 rpm and a chopper speed of rotation between 200 and 800 rpm. The vacuum drying systems used according to EP 0 753 306 are sold for example by the former companies Firmen Inox Glatt AG or Inox-Maurer AG under the names "IUT" or "INOX". Current manufacturers and distributors include, for example, De Dietrich Process Systems GmbH, Mainz, Germany (Rosemund®).

With this vacuum drying system, the fluid extract to be dried is pumped from above into the mixing and drying chamber in the batch method and is then subjected to a vacuum.

A preferred vacuum drying system comprises the following features, as are implemented for example in a known IUT/INOX system (see above):

a.) A multi-branched stirrer extending through a cylindrical mixing and drying chamber and having its own drive and, depending on requirements, vapour filter, backwash device, solvent condenser with aftercooler and collection vessel, back-condenser, a process, control and regulation unit, and optionally granulation nozzles.

b.) Furthermore, a chopper extending over the entire depth of the drying and mixing chamber and having a drive independent of the stirrer may be provided as well as optionally a comb-like stator for increasing the chopper effect.

c.) Furthermore, one or more nozzles may optionally be provided in order to introduce the liquid plant extract from a reservoir into the drying chamber, for example as described in WO2002073108.

The dry plant extracts obtained in this way are processed further to form pharmaceutical preparations.

The agent having an antimicrobial effect, containing the dry plant extract according to the invention, can thus advantageously be used in the treatment of infections triggered by pathogens relevant to the airways. The expectorant and anti-inflammatory effect is supplemented by the additional antimicrobial effect. An infection of the upper airways is thus confined or even completely stopped in addition to the loosening of the viscous mucus charged with pathogens, weakened by killing and/or reduction of the proliferation of the bacterial pathogens.

Due to the above-described invention, a patient suffering from sinusitis and/or rhinosinusitis and/or inflammation of the nasal sinuses for example, in particular in the acute form in each case, is treated in a gentle manner without the use of synthetic-chemical components.

The (pharmaceutical) composition of the present invention having an antimicrobial effect is particularly effective against pathogens relevant to the airways, wherein it has demonstrated antimicrobial efficacy specifically against gram-positive cocci, such as *Staphylococcus aureus, Staphylococcus aureus* (MRSA), *Staphylococcus epidermidis, Streptococcus pyogenes, Streptococcus pneumoniae* and *Streptococcus mutans*, against gram-negative bacilli, such as *Haemophilus influenzae*, and against *Enterobacteriaceae faecalis*. Efficacy against viruses is also achieved.

The galenic formulation of the antimicrobial agent can be selected from the group consisting of: drops, juice, syrup, tablets, dragées, capsules, retard formulations, rectal or vaginal suppositories, infusions, in particular throat sprays and disinfection solutions; ointments, emulsions, granulates, powders, nose sprays, liquid or solid preparations for inhalation, compresses, waddings, in particular wound and gum dressings, tamponades, including for teeth, rinsing solutions, in particular in combination with physiological and hyperosmolar concentrations of salts or salt mixtures, preferably table salt, in particular sea salt. Of course, the formulation can contain pharmaceutically conventional auxiliary agents.

The present invention therefore also relates to the use or application of the antimicrobial agent according to the invention containing a dry plant extract according to the invention for treatment of infections triggered by pathogens relevant to the airways, and to the use for production of a pharmaceutical, and also to a pharmaceutical as such.

In a further embodiment, the invention relates to a pharmaceutical for use or application in the case of sinusitis and/or rhinosinusitis and/or inflammation of the nasal cavities, in particular in the acute form in each case, in particular for treatment and prophylaxis of sinusitis and/or rhinosinusitis and/or inflammation of the nasal sinuses, in particular in the acute form in each case.

Due to the ENO relevance of the tested pathogens, the agent according to the invention is likewise outstandingly suitable in any instance in which bacteria can be fought directly and immediately locally or topically.

The agent according to the invention can thus preferably be used (in addition to the systemic application) directly at the contaminated location, for example in the form of a disinfection solution to be biologically degraded 100%, or of course also for direct topical application to skin and mucous membranes both in humans and in animals. Different forms of the application are considered for this purpose. The formulations are particularly suitable as solutions, creams, ointments and emulsions in the dermatological field of human and also veterinary medicine. Here, the agent according to the invention can be applied directly to the diseased part of the skin and/or can be used in the form of saturated compresses, waddings or tamponades.

Of course, the application of the agent according to the invention in the overall field of diseases of the entire respiratory tract, in particular of the upper airways, here preferably in the region of throat, nasal and nasal sinus mucous membranes, is of particular interest. Nasal rinsing, in particular in conjunction with salts, for example in combination with a physiological or hyperosmolar salt solution, is of particular significance. In accordance with the invention, a nasal spray containing the agent according to the invention is also included.

The broad range of new application possibilities reaches from tonsil paint solutions and gargling solutions in the case of pharyngeal infections to powder inhalation preparations or nebulizer inhalation preparations.

Further fields of application and indication comprise wound and gum dressings, for example in the form of cotton waddings or cotton yarn waddings, which are saturated with the agent according to the invention. Ear rinses with solutions that contain the agent according to the invention are also conceivable in the case of infections of the ear canal.

The invention therefore likewise relates to a pharmaceutical for use and application of diseases of the entire respiratory tract, in particular of the upper airways, in particular in the region of the throat, nasal and nasal sinus mucous membranes, respiratory diseases, in particular mucoviscidosis (cystic fibrosis), in particular the treatment and prophylaxis thereof. Mucoviscidosis can particularly advantageously be treated, see FIGS. 7A and 7B.

A further preferred embodiment concerns a dietary supplement containing the agent according to the invention, in particular in the form of a dietary composition. Suitable foods or foodstuffs, including water, according to the invention are those as defined (although not definitively) for example in regulation (EC) No. 178/2002 of 28 Jan. 2002, such as bakery products and beverages and infant food preparations. The dietary supplement according to the invention can be mixed with a suitable physiologically compatible carrier.

The pharmaceutical preparations according to the invention can be produced in the form of dosage units. This means that the preparations may be present in the form of individual parts, for example capsules and ampoules, of which the active ingredient content of dry plant extracts corresponds to a fraction or a multiple of an individual dose. The dosage units may contain, for example, 1, 2, 3 or 4 single doses or ½, ⅓ or ¼ of a single dose. A single dose preferably contains the amount of dry plant extract (active ingredient) according to the invention that is administered in one application and that usually corresponds to the entire daily dose or one half, one third or one fourth of a daily dose. A dosage of three times daily, preferably in the form of a tablet, in particular in the morning, afternoon and evening, possibly at meal times, is preferred.

In a further preferred embodiment, the galenic formulation of a calcium coated tablet can be selected, as disclosed in EP1392337.

Non-toxic, inert pharmaceutically suitable carrier substances are to be understood to include solid, semi-solid or liquid diluting agents, fillers and formulation aids of any type, such as a) fillers and diluting agents, for example starches, lactose, cane sugar, glucose, mannite, dextrins, maltodextrin and silicic acid, highly dispersed silicon dioxide, b) binders, for example carboxymethyl cellulose, cellulose powder, microcrystalline cellulose, alginates, gelatines, polyvinylpyrrolidone, c) humectants, for example glycerol, d) splitting agents, for example agar-agar, calcium carbonate and sodium carbonate, e) dilution restrainers, for example paraffin, and f) resorption accelerators, for example quaternary ammonium compounds, g) wetting agents, for example cetyl alcohol, glycerol monostearate, h) adsorption agents, for example kaolin and bentonite, and i) lubricants, for example talc, calcium stearate and magnesium stearate, and solid polyethylene glycols or mixtures of the substances listed under a) to i).

The tablets, dragées, capsules, pills and granulates may be provided with the conventional coatings and coverings, optionally containing opacity promoting agents, for example such as, although not definitively, hypromellose, microcrystalline cellulose, stearic acid, titanium dioxide, and may also be composed such that they release the active ingredient(s) only, or preferably, in a certain part of the intestinal tract, in a delayed manner where necessary, wherein polymer substances and waxes for example may be used as embedding matter.

EXAMPLES

These examples are intended merely to explain the invention, without limiting the invention to these examples.

Hereinafter, "dry extract (TE)" means the dry plant extract produced according to the invention.

Example 1

The antiviral activity of the dry extract according to the invention was confirmed in a number of in vitro tests.

In these tests, the general cell-damaging (cytotoxic) effect of the dry extract according to the invention compared to the known product Sinupret® (alcoholic/aqueous) was initially tested. After incubation of suitable cell lines (for example HeLa, HEp-2) with different viruses over a period of one hour, the infected cell lines were treated with different concentrations, and the effect on the virus proliferation was then measured.

The antiviral activity was determined quantitatively in vitro via the detection of a cytopathogenic effect (Adeno5 Virus), in a plaque reduction assay (FluA, HRV14, RSV) and in virus-specific enzyme immunoassays (ELISA; Adeno5, RSV).

In the event of detection of a cytopathogenic effect, the virus-sensitive cells grown confluently were infected with a defined virus solution (M.O.I., multiplicity of infection). After incubation for one hour, the virus inoculum was drawn off and the infected cell layers were washed. The physiological substance concentrations were then added. The respective test batches were cultivated until a 70-90% cytopathogenic effect (CPE), which presents itself as a destroyed cell region, was observed under microscope in the untreated virus controls. The area of the destroyed cell region was defined as 100% infection. Comparatively, the cell areas of the respective test batches were evaluated so that inhibiting effects of the substances to be analysed can be shown as an inhibition percentage (% inhibition).

In the case of the plaque reduction assay, the virus-sensitive cells grown confluently were infected with a defined virus solution (M.O.I., multiplicity of infection). After incubation for one hour, the virus inoculum was drawn off and the infected cell layers were washed. The physiological substance concentrations and also a solid medium component (agarose or methylcellulose) were then added, followed by further incubation. The infection area was delimited by the solid component in the superimposed medium, such that a series of infected cells ("plaque") was produced. The respective test batches were cultivated until the set plaque number (M.O.I.) was observed under microscope in the untreated virus controls. By fixing and dyeing the cell layer, the virus plaque can be made visible as light rings in the dark-coloured cell layers. The plaque number was determined with the aid of image processing systems. The plaque number of the untreated control was defined as 100% infection. By contrast, the plaque number of the respective test batches was evaluated such that inhibitory effects of the test substance can be presented as an inhibition percentage (% inhibition).

The virus production was analysed by ELISA. Test strips with antibodies against the specific viruses bind the viruses found in the cell culture supernatant of the infected cell lines. In order to make the reaction visible, a pathogen-specific detection antibody labelled with peroxidase was introduced. After addition of a substrate/chromogen and also of hydrogen peroxide and tetramethylbenzidine, a colour reaction takes place. The intensity of the colouration was determined photometrically and was proportional to the content of virus antigen. The virus production in the case of infected and treated cells was analysed after infection of virus-sensitive cells grown confluently with a defined virus solution (M.O.I., multiplicity of infection). After incubation for one hour, the virus inoculum was drawn off and the infected cell layers were washed. The physiological substance concentrations were then added. The respective test batches were cultivated until a 70-90% cytopathogenic effect (CPE) was observed under microscope in the untreated virus controls. The newly synthesized viruses were located in this stage in the cell culture supernatant. The photometrically determined extinction values of the untreated controls were defined as 100% infection. By way of comparison, the extinction values of the respective test batches were evaluated, such that inhibitory effects of the test substances can be presented as an inhibition percentage (% inhibition).

A significant inhibition of the virus proliferation, that is to say a reduction of the virus load, was demonstrated in all tests (see FIG. 1).

Figure 2:
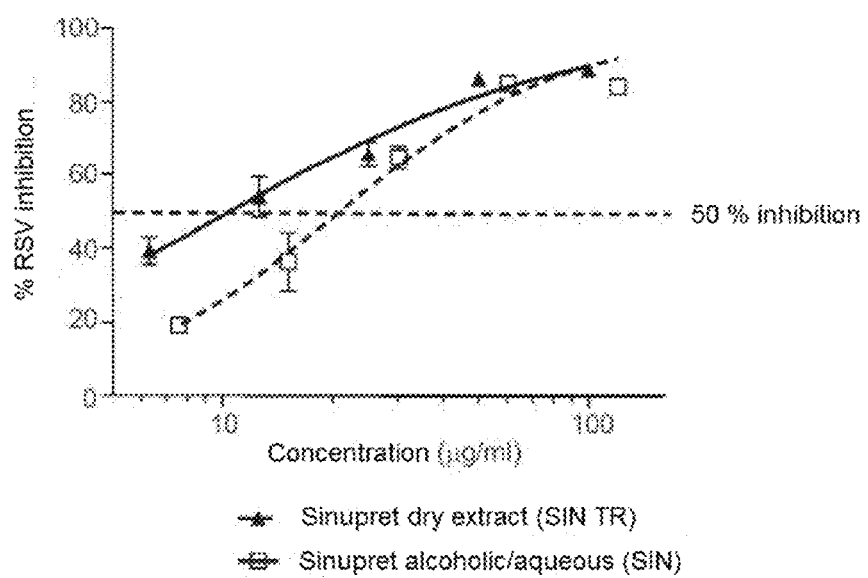
FIG. 2 shows the inhibition of respiratory virus proliferation.

The dry extract according to the invention inhibits the proliferation of human (FluA) and pig (pFluA) influenza viruses (flu viruses). Concentrations of 124.8 μg of Sinupret/ml (FluA) and of 43.4 μg of Sinupret/ml (pFluA) are sufficient in order to inhibit (reduce) the virus (load) by 50%. The Sinupret dry extract according to the invention demonstrated a lower EC50 against virus strains HRV 14, Adeno5 and RSV, and therefore accordingly a greater efficacy compared to Sinupret® alcoholic/aqueous (see FIGS. 1 and 2).

TABLE 0 antiviral effect

| Virus strain | Sinupret alcoholic/aqueous EC50 [μg/ml] | Sinupret dry extract EC50 [μg/ml] |
|---|---|---|
| HRV 14 | 73.1 | 50.5 |
| Adeno 5 | 66.4 | 13.8 |
| RSV | 20.7 | 10.4 |

Example 2

The anti-inflammatory activity of Sinupret could be confirmed in the animal model. For example, carrageen-induced paw oedema in rats (Male Wistar Han rats, 220-230 g) was selected as the test model. In this model, it was possible to examine the anti-inflammatory effect of test substances by measuring their inhibitory effect on the paw oedema or pleuritis caused by carrageen. The following were used as reference substances: (RS)-2-[4-(2-methylpropyl)phenyl]propanoic acid (Ibuprofen®) and 2-[1-(4-chlorobenzoyl)-5-methoxy-2-methyl-1H-indol-3-yl]acetic acid (indomethacin, "indo"). In the present tests, groups of 10 rats in each case were treated either with Ibuprofen®, indomethacin, Sinupret® dry extract (SIN TR) or Sinupret® drug mixture (SIN, as commercially available) and were injected one hour later with carrageen. The inhibition of the oedema formation by the test and reference substances was determined at various moments in time after carrageen injection, wherein the paw volume of animals treated only with carrageen was used as a control (vehicle=blank control). The results of these tests are presented in Tables 1 and 2 and in FIGS. 3 to 6 and will be explained hereinafter.

Figure 3:
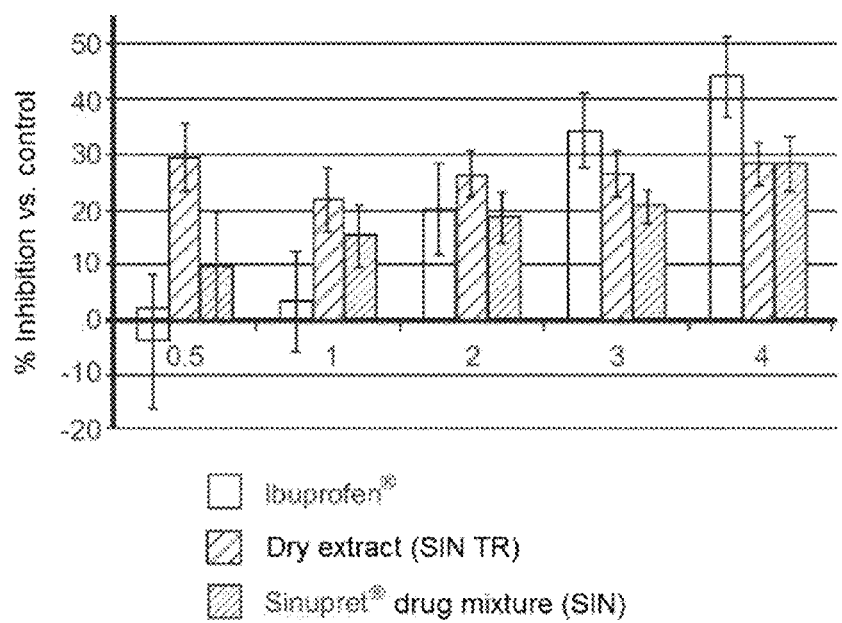
FIG. 3 shows the effect in the inflammation model.

FIG. 3: In the carrageen model, it was found that the dry extract according to the invention inhibits the paw oedema induced by carrageen after just 30 minutes following carrageen injection, and more specifically inhibits said paw oedema to a greater extent than the Sinupret drug mixture, where as Ibuprofen® still did not show any anti-inflammatory effect at this early moment in time. Even one and two hours after oedema induction, the anti-inflammatory effect of the dry extract according to the invention was still stronger than that of Ibuprofen® and Sinupret® drug mixture (SIN).

Table 1 shows the effect of Sinupret® (SIN) in the case of carrageen-induced pleuritis on the basis of the inflammatory markers ($PGE_2$, $LTB_4$, TNF alpha, IL1 beta) with measurement after 4 h.

Rats (10 per group) were each treated with 100 mg/kg or 500 mg/kg of SIN and by way of comparison with 5 mg/kg of indomethacin and blank and were injected 1 hour later with carrageen.

"Inflammatory cells" correlates to PMN (polymorphonuclear neutrophils) accumulation/infiltration.

Statistics: average+/−SEM, n=10, p<0.01; *p<0.001 vs vehicle (blank) (Tukey Test), p<0.05 is statistically significant.

Figure 4:
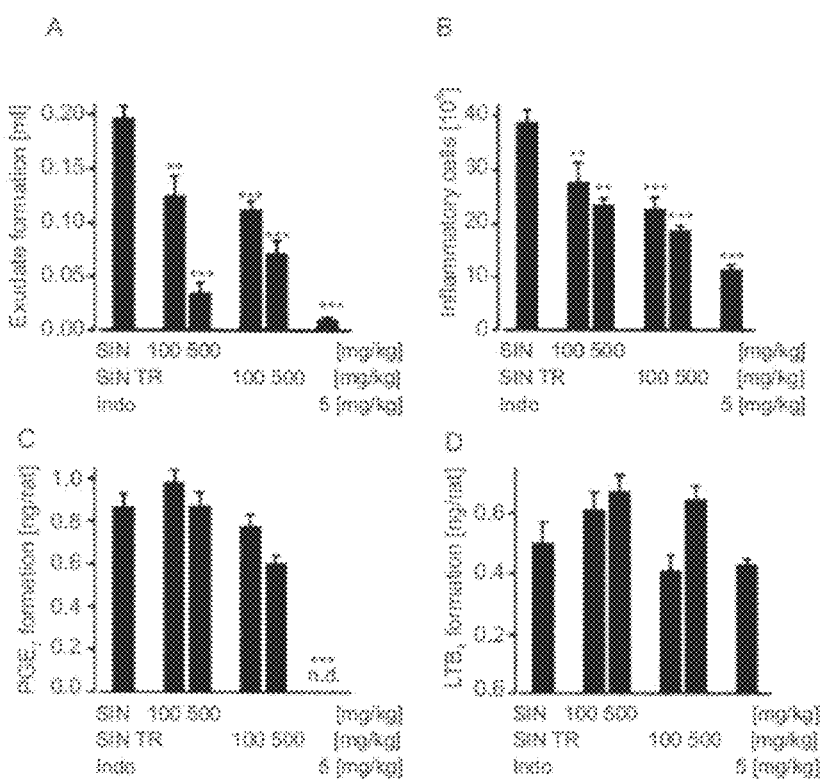
FIGS. 4A-4D show a comparative illustration by means of graphs.

A comparative illustration by means of graphs is provided in FIG. 4.

case with 30 μg of protein from rat lung (homogenized) on 10% SDS polyacrylamide gel and COX-2 was analysed.

Figure 6:
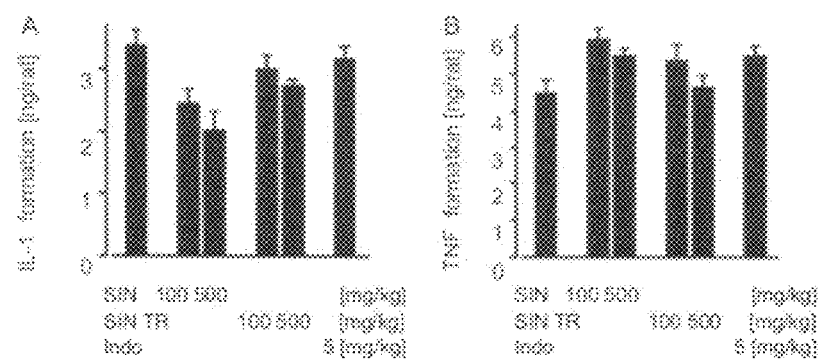
FIG. 6 shows the effect of Sinupret® drug mixture (SIN) and Sinupret dry extract (SIN TR) on cytokines.

FIG. 6 shows the effect of Sinupret® drug mixture (SIN) and Sinupret dry extract (SIN TR) on cytokines.

Rats (10 per group) were each treated with 100 mg/kg or 500 mg/kg of SIN or SIN TR and by way of comparison with 5 mg/kg of indomethacin and blank and were injected 1 hour later with carrageen. The inflammatory markers IL1 beta and TNF alpha were determined 4 h after carrageen injection.

Statistics: average+/−SEM, n=10, p<0.01; *p<0.001 vs vehicle (blank) (Tukey Test), p<0.05 is statistically significant.

Conclusion:

The Sinupret dry extract (SIN TR) according to the invention demonstrated, at least for PGE2, a particularly

| treatment | exudate volume (ml) | Inflammatory cells × 10$^6$ | $PGE_2$ ng/rat | $LTB_4$ ng/rat | TNFα ng/rat | IL1β ng/rat |
| --- | --- | --- | --- | --- | --- | --- |
| vehicle | 0.196 ± 0.012 | 38.6 ± 2.54 | 0.861 ± 0.061 | 0.50 ± 0.07 | 4.94 ± 0.33 | 3.37 ± 0.25 |
| Sinupret® 100 mg/kg | 0.125 ± 0.018 ** (36%) | 27.7 ± 2.61 ** (28%) | 0.973 ± 0.066 | 0.61 ± 0.06 | 5.94 ± 0.30 | 2.45 ± 0.23 (27%) |
| Sinupret® 500 mg/kg | 0.034 ± 0.010 *** (83%) | 23.5 ± 1.34 *** (39%) | 0.865 ± 0.065 | 0.67 ± 0.06 | 5.48 ± 0.19 | 2.03 ± 0.30 ** (40%) |
| Indometharin 6 mg/kg | 0.009 ± 0.003 *** (96%) | 11.4 ± 0.93 *** (70%) | <0.125 *** | 0.43 ± 0.02 | 5.48 ± 0.28 | 3.17 ± 0.18 |

Table 2 shows the effect of Sinupret® dry extract (SIN TR) in the case of carrageen-induced pleuritis on the basis of the inflammatory markers ($PGE_2$, $LTB_4$, TNF alpha, IL1 beta) with measurement after 4 h.

Rats (10 per group) were each treated with 100 mg/kg or 500 mg/kg of SIN TR and by way of comparison with 5 mg/kg of indomethacin and blank and were injected one hour later with carrageen.

"Inflammatory cells" correlated with PMN (polymorphonuclear neutrophils) accumulation/infiltration.

Statistics: average+/−SEM, n=10, p<0.01; *p<0.001 vs vehicle (blank) (Tukey Test), p<0.05 is statistically significant.

advantageous significant inhibition of PGE2 formation (30%; p<0.01; FIG. 4C, Table 2) compared to Sinupret® drug mixture (SIN). Furthermore, the Sinupret dry extract (SIN TR) according to the invention is more effective at lower dosage compared to the known Sinupret® drug mixture (SIN).

Example 3

The following example shows that the dry extract according to the invention, with topical use, activates chloride secretion, most likely via the activation of CFTR. In addition, the dry extract according to the invention stimulates the ciliary beat frequency.

| treatment | exudate volume ml | Inflammatory cells ×10$^6$ | $PGE_2$ ng/rat | $LTB_4$ ng/rat | TNFα ng/rat | IL1β ng/rat |
| --- | --- | --- | --- | --- | --- | --- |
| vehicle | 0.196 ± 0.012 | 38.6 ± 2.54 | 0.861 ± 0.061 | 0.50 ± 0.07 | 4.94 ± 0.33 | 3.37 ± 0.21 |
| dry extract 100 mg/kg | 0.112 ± 0.009 *** (43%) | 22.8 ± 2.19 *** (41%) | 0.775 ± 0.050 (10%) | 0.41 ± 0.05 | 5.36 ± 0.44 | 3.00 ± 0.21 (11%) |
| dry extract 500 mg/kg | 0.072 ± 0.013 *** (63%) | 18.8 ± 0.92 *** (51%) | 0.603 ± 0.039 ** (30%) | 0.64 ± 0.05 | 4.66 ± 0.30 | 2.74 ± 0.09 (19%) |
| Indometharin 6 mg/kg | 0.009 ± 0.003 *** (96%) | 11.4 ± 0.93 *** (70%) | <0.125 *** | 0.43 ± 0.02 | 5.48 ± 0.28 | 3.17 ± 0.18 |

A comparative illustration by means of graphs is provided in FIG. 4.

Figure 5:
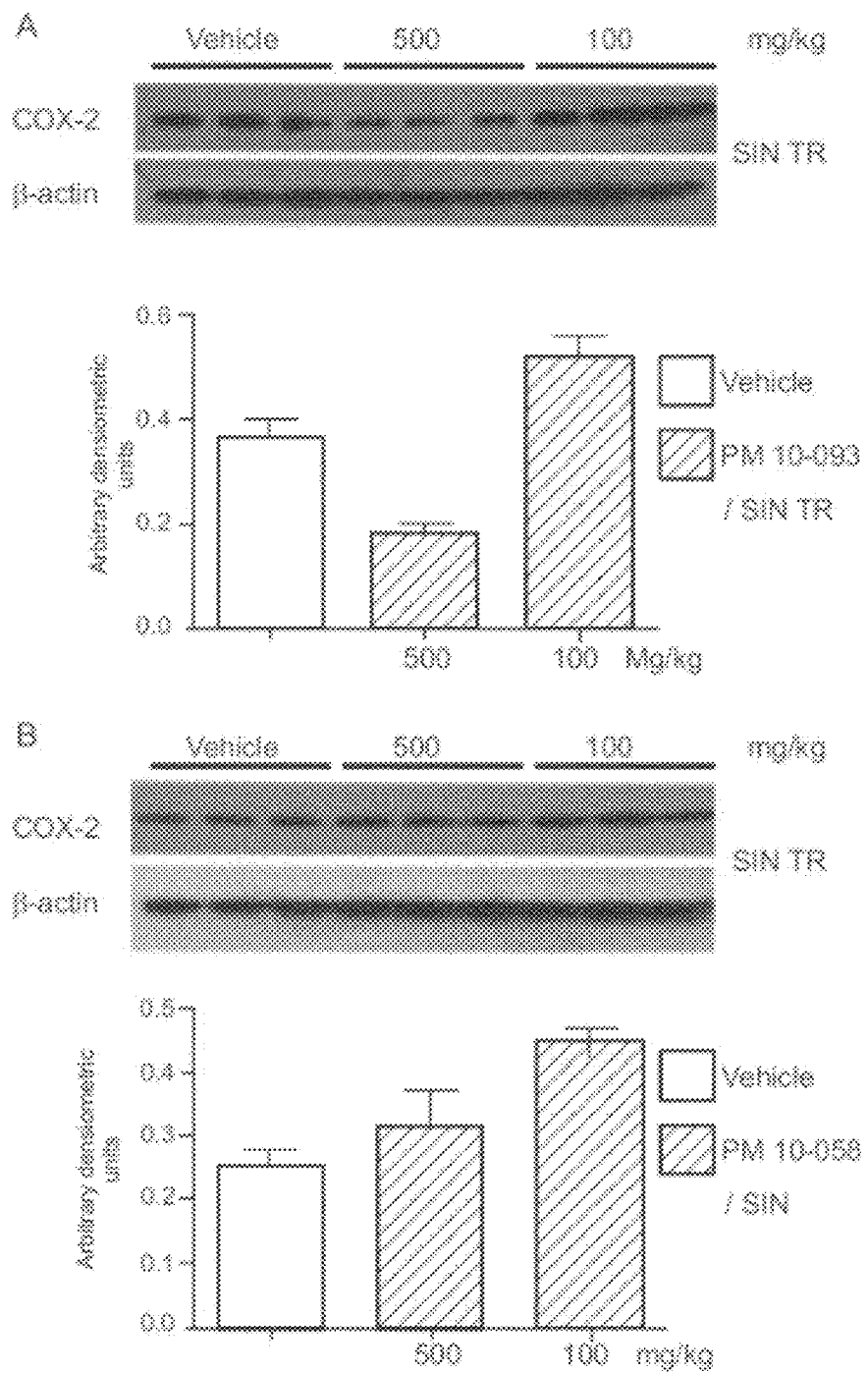
FIG. 5 shows the effect of Sinupret® drug mixture (SIN) and of Sinupret dry extract (SIN TR) on the expression of COX-2 protein in the rat lung.

FIG. 5 shows the effect of Sinupret® drug mixture (SIN) and of Sinupret dry extract (SIN TR) on the expression of COX-2 protein in the rat lung.

Rats (10 per group) were each treated with 100 mg/kg or 500 mg/kg of SIN or SIN TR and by way of comparison with 5 mg/kg of indomethacin and blank and were injected 1 hour later with carrageen. A western blot was carried out in each Material: cell culture: human bronchial epithelial cells (HBE) were acquired from Lonza (Walkersville, Md.) and were expanded with bronchial epithelial cell growth medium (BEGM) from Lonza (Walkersville, Md.). 250 mg of dry extract according to the invention were dissolved in 1 ml of 50% ethanol and were treated by ultrasound at 35 kHz for 30 minutes with subsequent centrifugation at 3,000 g for 10 minutes at room temperature. The supernatant was suctioned off. Amiloride (Sigma, St. Louis, Mo.) was dissolved in distilled deionized water and diluted 1,000 times. Forskolin (Kaliokemm, EMD, San Diego, Calif.) was dissolved in DMSO and diluted 1,000 times.

An Ussing chamber (Physiology Instruments San Diego, Calif., USA) was used, containing Transwell inserts (Corning Life Sciences) with implementation at 37 degrees and a monolayer with a voltage terminal of 0 volts (VCC 600) (Physiology Cal Instruments San Diego, Calif., USA) after setting of the forward resistance. Transwell filters were placed in the solution at 37 degrees and the solution was infused continuously with 95% oxygen to 5% $CO_2$. The transepithelial resistance (RT) was adjusted using a computer program (Physiology Instruments San Diego, Calif., USA) at 640 ms, bipolar 10 mV potential via the monolayer measured in accordance with Ohms Law. By definition, a positive result is an anion secretion or cation absorption. The experiments were repeated at least 3 times in HBE cell cultures.

Used electrolyte solution (in mM): 120 NaCl, 25 $NaHCO_3$, 3.3 $KH_2PO_4$, 0.8 $K_2HPO_4$, 1.2 $MgCl_2$, 1.2 $CaCl_2$ and 10 glucose.

The cilial beat frequency (CBF) measurements were carried out in accordance with a method according to Woodworth et al (Woodworth, B A, Zhang S, Tamashiro E, Zinc increases ciliary beat frequency in a calcium dependent manner, Am J Rhinol Allergy 24: 6-10, 2010). The images were created by Leica Microsystems, Inc., Bannockburn, Ill. with a 63× lens (model A 602f-2, high-speed monogram digital video camera, Basler AG, Ahrensburg, Germany). The dry extract according to the invention was examined for transepithelial electrolyte transport. The dry extract was applied in increasing concentration amounts to the basolateral surface of HBE cells in the Ussing chamber, before subsequent addition of amiloride and forskolin.

Figure 7A:
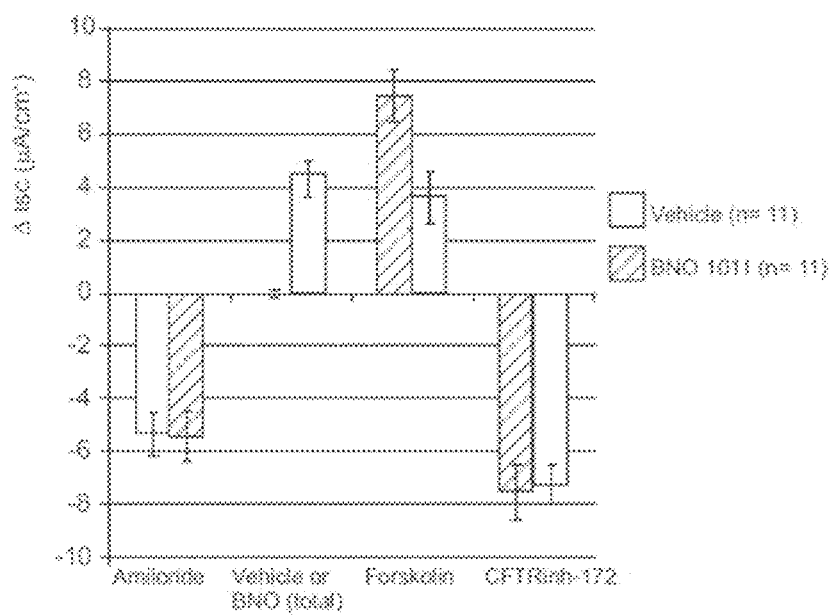
FIG. 7A shows that the dry extract according to the invention demonstrates a change of the transepithelial short-circuit current (ISC) after addition of the amiloride and forskolin.
Figure 7B:
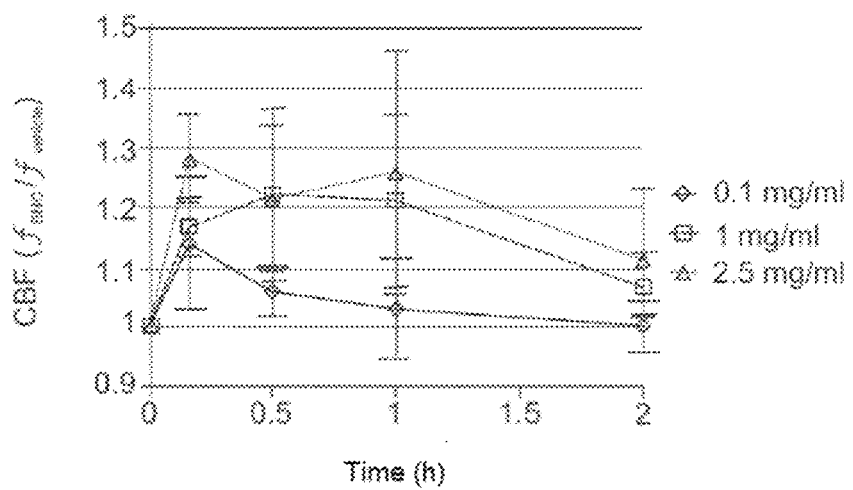
FIG. 7B shows that a dose-dependent rise in the cilial beat frequency (CBF) measurements can be observed, which is accompanied by a chloride ion secretion.

In FIGS. 7a and 7b, the dry extract according to the invention demonstrates a change of the transepithelial short-circuit current ($I_{SC}$) (7A) after addition of amiloride and forskolin, such that a dose-dependent rise in the cilial beat frequency (CBF) measurements can be observed (7B), which is accompanied by a chloride ion secretion.

These results prove the advantageous use of the dry extract according to the invention, for example by means of a nasal spray, since improved mucociliary clearance (MCC) can be achieved.

Conclusion: The dry extract according to the invention is suitable for the treatment of respiratory diseases, in particular for the treatment of mucoviscidosis (cystic fibrosis).

Example 4

The anti-inflammatory effect of the Sinupret dry extract according to the invention and Sinupret drops (alcoholic/aqueous ("Sinupret OD")) was examined as follows.

Carrageen-induced paw oedema (see above): The test animals (n=8/group) were weighed in the fasted state and the basal volume of the rear paw was measured. The animals were fed the test substances (10 mL/kg of body mass) (Sinupret dry extract (TE): 5 mg/kg, equivalent to the amount of drug mixture in 1 mL of drops/kg; 50 mg TE/kg corresponding to 1 times the human equivalent dose (1×HED); Sinupret drops (Sinupret OD): 1 mL OD/kg, corresponding to 1 times the human equivalent dose (1×HED); 2.5 mL OD/kg, equivalent to the amount of drug mixture in 50 mg TE/kg; indomethacin: 20 mg/kg as a positive control; 10% v/v ethanol as vehicle control). After 60 minutes, the animals were provoked by a subcutaneous injection of carrageen (0.1 mL of a 1% w/v solution in physiological table salt solution) into the left rear paw (in a plantar manner). Paw volumes were determined in all animals by means of plethysmography before (−1 h) and after carrageen injection (study 1: +1 h (FIG. 8), study 2: +15 min, +30 min, +1 h (FIG. 9)). The inhibition percentage of paw swelling vs. vehicle control was calculated individually for each test animal.

Figure 8:
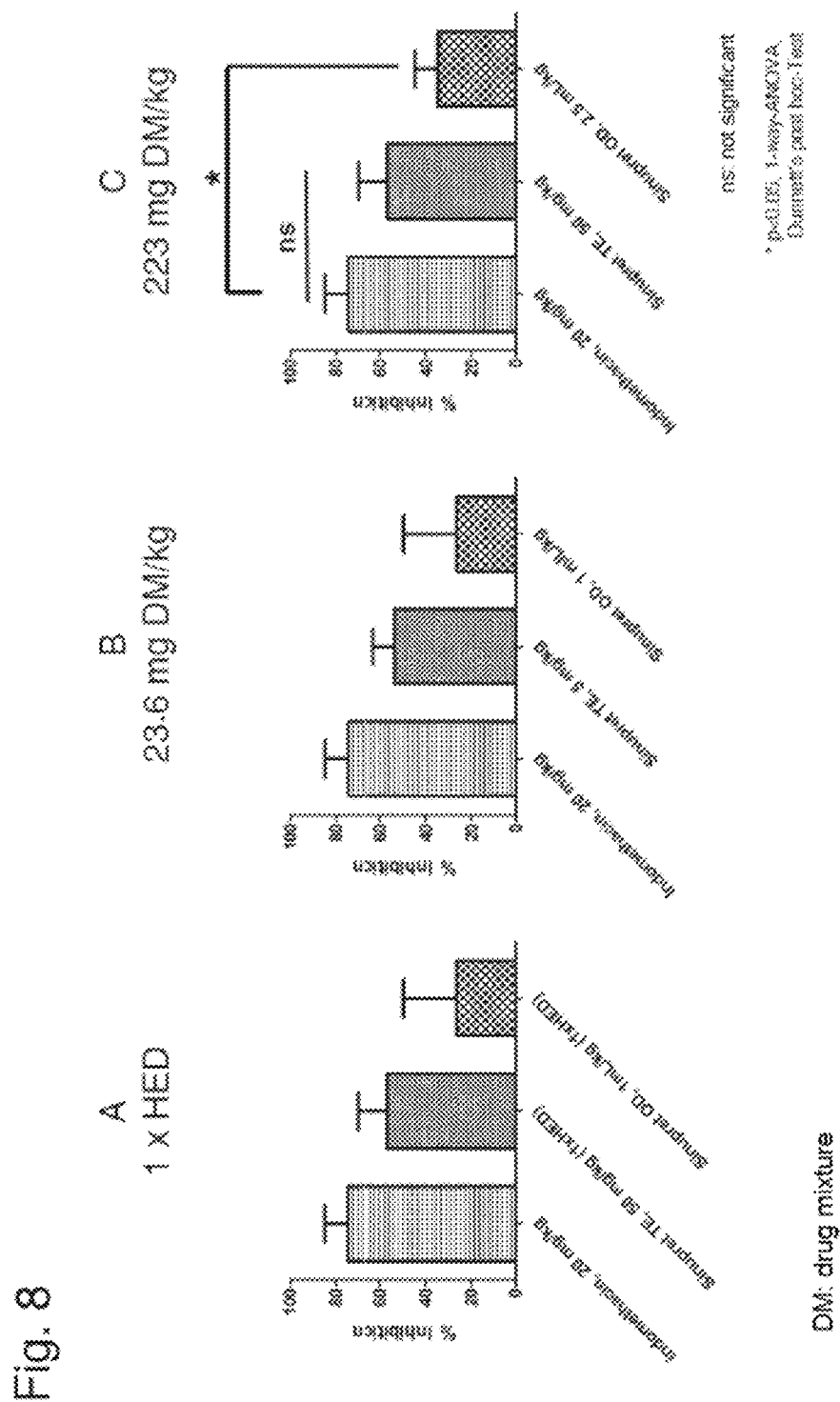
FIG. 8 shows paw volumes determined in all animals by means of plethysmography before (−1 h) and after carrageen injection (+1 h).

The results are shown by way of comparison in FIG. 8 (inhibition of inflammation after 1 hour).

FIG. 8: A: Sinupret TE and Sinupret OD were each administered in a dose equivalent to 1 times the human equivalent dose. Sinupret TE has a quicker and stronger anti-inflammatory effect than Sinupret OD. The inhibition of inflammation by Sinupret TE, not by Sinupret OD, is comparable after 1 h with the inhibitory effect of the known antiphlogistic indomethacin.

B, C: The dose administered here of Sinupret TE and Sinupret OD is comparable based on the respective amount of drug mixture (DM) used for production (B: 23.6 mg/kg, C: 223 mg/kg). Sinupret TE has a quicker and stronger anti-inflammatory effect compared to Sinupret OD. The inhibition of inflammation produced by Sinupret TE, not by Sinupret OD, is comparable after 1 h with the inhibitory effect produced by the known antiphlogistic indomethacin.

Figure 9:
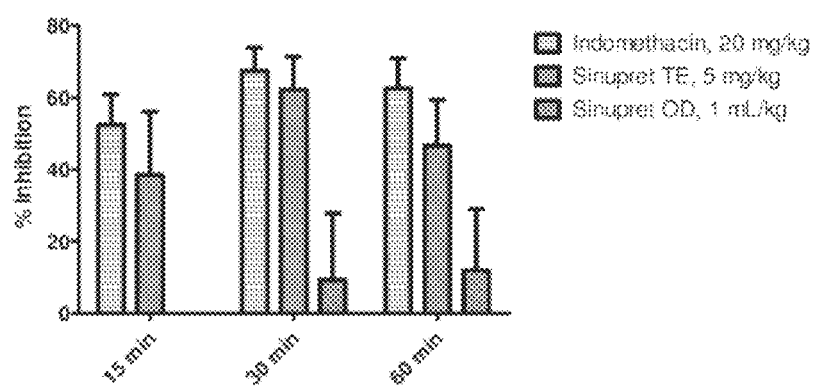
FIG. 9 shows paw volumes determined in all animals by means of plethysmography before (−1 h) and after carrageen injection (+15 min., +30 min., and +1 h).

The results are shown by way of comparison in FIG. 9 (inhibition of inflammation after +15 min, +30 min, +1 h).

FIG. 9: the administered dose of Sinupret TE and Sinupret OD is comparable based on the respective amount of drug mixture used for production (23.6 mg of drug mixture/kg). Sinupret TE is characterized by an earlier and stronger onset of action compared to Sinupret OD. Sinupret OD only inhibits inflammation from 30 min. Sinupret TE inhibits inflammation comparatively strongly and quickly over the entire period of time tested in a manner comparable to the known antiphlogistic indomethacin.

Example 5

The following example describes specific marker compounds from the multi-substance mixture.
Implementation:
All samples were extracted immediately after the individual extraction steps, were filtered and were analysed by mass spectrometry in a concentration of 600 mg/L (in 30 vol. % MeOH). Methylparaben was used as an internal standard. The samples were processed twice and analysed twice. The following parameters and devices were used:
MS: 5600 Triple ToF (ABSciex); HPLC: Agilent 1290
Software: Analyst TF 1.5.1, MultiQuant 2.1.1, MarkerView 1.2.1
Stationary phase: Zorbax RRHD Eclipse Plus C18, 2.1×50 mm, 1.8 μm
LC Method:

| Step | Time (min) | Flow rate (μL/min) | Eluent A | Eluent B |
|---|---|---|---|---|
| 0 | 0.00 | 600 | 95.0 | 5.0 |
| 1 | 1.00 | 600 | 95.0 | 5.0 |
| 2 | 6.00 | 600 | 69.0 | 31.0 |
| 3 | 10.00 | 600 | 0.0 | 100.0 |
| 4 | 11.00 | 600 | 0.0 | 100.0 |
| 5 | 11.10 | 600 | 95.0 | 5.0 |
| 6 | 13.00 | 600 | 95.0 | 5.0 |

A = 0.1% of formic acid in H2O;
B = acetonitrile

MS Method:

| Scan Type | negative |
| --- | --- |
|  | TOF MS |
| Duration | 10.997 mins |
| Cycle Time | 0.2750 secs |
| GS1 (Spray Gas): | 70.00 |
| GS2 (Turbo Gas): | 55.00 |
| CUR (Curtain Gas): | 25.00 |
| TEM (GS 2): | 500.0 |
| ISVF (Ion Spray Voltage Floating): | 4500.0 |
| CAD (Collision Gas): | 6 |
| TOF Masses (Da): | 130-2000 |
| Accumulation Time (sec): | 0.25 |
| Time Bins to sum: | 4 |
| DP: | −100.0 |
| CE: | −10.0 |

TABLE 3 selective enrichment and depletion of characteristic ingredients

|  |  | m/z = 399.2 RT = 0.5 min | m/z = 540.3 RT = 8.4 min | m/z = 279.2 RT = 9.6 min |
| --- | --- | --- | --- | --- |
| Lab batch | 1st extraction (59 vol. % EtOH) | 8% | 2879% | 737.2 g (±11.7 g) |
|  | 2nd extraction (water) | 224% | 61% | 0.0 g |
|  | total extract | 100% | 100% | 622.3 g (±6.0 g) |
| Production batch | 1st extraction (59 vol. % EtOH) | 16.5% | 896% | 745.5 g (±19.6 g) |
|  | 2nd extraction (water) | 67% | 104% | 0.0 g |
|  | total extract | 100% | 100% | 119.9 g (±12.2 g) |

In so far as quantified via reference standards, the quantities of ingredients are specified as absolute content in [g]. Otherwise, the content of ingredients is specified in relation [%] to the respective total extract (after step f.)). The data originate from a lab batch A1 and a production batch P1. The signals were detected with negative ionisation.

TABLE 4 ingredients with typical enrichment in the first extraction step with increase by subsequent aqueous extraction.

|  |  | m/z = 401.1 RT = 2.6 min | m/z = 463.1 RT = 3.7 min | m/z = 623.2 RT = 3.9 min |
| --- | --- | --- | --- | --- |
| Lab batch | 1st extraction (59 vol. % EtOH) | 500.7 g (±6.4 g) | 122.0 g (±2.3 g) | 575.6 g (±6.4 g) |
|  | 2nd extraction (water) | 152.3 g (±3.6 g) | 11.9 g (±0.4 g) | 91.2 g (±0.1 g) |
|  | total extract | 655.4 g (±3.3 g) | 134.2 g (±0.8 g) | 657.6 g (±17.4 g) |
| Production batch | 1st extraction (59 vol. % EtOH | 704.5 g (±6.1 g) | 127.6 g (±3.0 g) | 527.0 g (±12.5 g) |
|  | 2nd extraction (water) | 70.0 g (±0.03 g) | 9.0 g (±0.02 g) | 42.3 g (±1.7 g) |
|  | total extract | 788.2 g (±11.8 g) | 138.1 g (±0.7 g) | 571.1 g (±20.2 g) |

In so far as quantified by reference standards, the quantities of ingredients are specified as absolute content in [g]. Otherwise, the content of ingredients is specified in relation [%] to the respective total extract (after step f.)). The data originate from the lab batch A1 and from the production batch P1. The signals were detected with negative ionization.

The invention claimed is:

1. A method for producing a dry plant extract mixture, said method comprising the following steps:

a) a first extraction of *Rumicis herba, Verbena officinalis, Sambucus nigra, Primula veris* and *Gentiana lutea* with water/alcohol to produce a first supernatant;

b) separating of the first supernatant to form a residue;

c) a second aqueous extraction of the residue to form a second supernatant;

d) separation of the second supernatant;

e) combining the first and second supernatant; and f) drying of the first and second supernatant to form the dry plant mixture.

2. The method of claim 1, wherein the ratio in step a.) of *Gentiana lutea:Rumicis herba:Verbena officinalis:Sambucus nigra:Primula veris* is 1:3:3:3:3.

3. The method of claim 1, wherein, in step a.), the water/alcohol has a content of 40:60 (v/v) to 60:40 (v/v) water/alcohol.

4. The method of claim 1, wherein, in step a.), the water/alcohol has a content of 41:59 (v/v) water/alcohol.

5. The method of claim 1, wherein, in step a.), the water/alcohol has a content of 50:50 (v/v) water/alcohol.

6. The method of claim 1, wherein the water/alcohol comprises ethanol.

7. The method of claim 1, wherein the water/alcohol comprises 96% ethanol.

8. The method of claim 1, wherein the plants in a.) are provided together in a batch.

9. The method of claim 1, wherein the extraction in steps a.) and c.) is carried out at 20 to 40° C.

10. The method of claim 1, wherein the extraction in steps a.) and c.) is carried out in 2 to 8 h.

11. The method of claim 1, wherein the drying process of step f.) is carried out under vacuum at 30 to 60° C.

12. The method of claim 1, wherein the drying process of step f.) is carried out under vacuum at 40 to 50° C.

13. The method of claim 1, wherein the drying process of step f.) is carried out in a vacuum agitated dryer.

* * * * *